(12) United States Patent
Mun et al.

(10) Patent No.: US 12,313,973 B2
(45) Date of Patent: May 27, 2025

(54) INSULATING LAYER FOR MULTILAYER PRINTED CIRCUIT BOARD, MULTILAYER PRINTED CIRCUIT BOARD COMPRISING SAME, AND METHOD FOR PRODUCING SAME

(71) Applicant: LG CHEM, LTD., Seoul (KR)

(72) Inventors: Jeong Wook Mun, Daejeon (KR); Kong Kyeom Kim, Daejeon (KR); Woo Jae Jeong, Daejeon (KR); Jee Hyeon Hwang, Daejeon (KR); Eun Byurl Cho, Daejeon (KR); Jeong Hyuk Ahn, Daejeon (KR)

(73) Assignee: LG CHEM, LTD., Seoul (KR)

( * ) Notice: Subject to any disclaimer, the term of this patent is extended or adjusted under 35 U.S.C. 154(b) by 653 days.

(21) Appl. No.: 17/632,815

(22) PCT Filed: Sep. 25, 2020

(86) PCT No.: PCT/KR2020/013031
§ 371 (c)(1),
(2) Date: Feb. 4, 2022

(87) PCT Pub. No.: WO2021/080203
PCT Pub. Date: Apr. 29, 2021

(65) Prior Publication Data
US 2022/0279663 A1  Sep. 1, 2022

(30) Foreign Application Priority Data

Oct. 24, 2019  (KR) .................. 10-2019-0132823
Sep. 22, 2020  (KR) .................. 10-2020-0122548

(51) Int. Cl.
| | |
|---|---|
| G03F 7/11 | (2006.01) |
| C07D 251/48 | (2006.01) |
| C07D 251/54 | (2006.01) |
| C08G 73/10 | (2006.01) |
| G03F 7/038 | (2006.01) |
| G03F 7/09 | (2006.01) |
| G03F 7/36 | (2006.01) |
| G03F 7/40 | (2006.01) |
| H05K 1/03 | (2006.01) |
| H05K 3/46 | (2006.01) |

(52) U.S. Cl.
CPC .............. *G03F 7/11* (2013.01); *C07D 251/48* (2013.01); *C07D 251/54* (2013.01); *C08G 73/1092* (2013.01); *G03F 7/094* (2013.01); *G03F 7/36* (2013.01); *G03F 7/40* (2013.01); *H05K 1/036* (2013.01); *H05K 3/4652* (2013.01)

(58) Field of Classification Search
CPC ... G03F 7/11; G03F 7/038; G03F 7/36; G03F 7/40; G30F 7/42
See application file for complete search history.

(56) References Cited

U.S. PATENT DOCUMENTS

| | | | | |
|---|---|---|---|---|
| 7,226,721 B2* | 6/2007 | Takei | .................. | G03F 7/091 430/326 |
| 2003/0190550 A1* | 10/2003 | Nitta | .................. | G03F 7/0392 430/311 |
| 2007/0292767 A1* | 12/2007 | Takei | .................. | H01L 21/0276 430/4 |

FOREIGN PATENT DOCUMENTS

| | | |
|---|---|---|
| CN | 1201586 A | 12/1998 |
| JP | 2010-002877 A | 1/2010 |
| JP | 2012-103537 A | 5/2012 |
| JP | 2013-237826 A | 11/2013 |
| JP | 2014-209260 A | 11/2014 |
| JP | 2015-131772 A | 7/2015 |
| JP | 201665012 A | 4/2016 |
| JP | 2017-039898 A | 2/2017 |
| JP | 2018530167 A | 10/2018 |
| JP | 2019-057527 A | 4/2019 |
| KR | 10-2017-0123703 A | 11/2017 |
| KR | 10-2018-0018333 A | 2/2018 |
| KR | 10-2018-0018337 A | 2/2018 |
| TW | 201823304 A | 7/2018 |
| WO | 2018030694 A1 | 2/2018 |

OTHER PUBLICATIONS

International Search Report issued for International Application No. PCT/KR2020/013031 on Jan. 7, 2021, 4 pages.
Kalyanaraman, S., et al. "Optical properties of melamine based materials." Optik 125.22 (2014): 6634-6636.

* cited by examiner

*Primary Examiner* — John S. Chu
(74) *Attorney, Agent, or Firm* — ROTHWELL, FIGG, ERNST & MANBECK, P.C.

(57) ABSTRACT

The present disclosure provides an insulating layer for a multilayer printed circuit board, a multilayer printed circuit board including the same, and a method for fabricating the same. The insulating layer of the present disclosure includes a polymer resin layer containing a melamine derivative, and thus may have excellent adhesion to a patterned metal layer.

15 Claims, 1 Drawing Sheet

INSULATING LAYER FOR MULTILAYER PRINTED CIRCUIT BOARD, MULTILAYER PRINTED CIRCUIT BOARD COMPRISING SAME, AND METHOD FOR PRODUCING SAME

BACKGROUND

1. Technical Field

This application is a 35 U.S.C. 371 National Phase Entry Application from PCT/KR2020/013031, filed on Sep. 25, 2020, which claims the benefit of the filing date of Korean Patent Application Nos. 10-2019-0132823 and 10-2020-0122548, filed in the Korean Intellectual Property Office on Oct. 24, 2019 and Sep. 22, 2020, respectively, all of the contents of which are incorporated herein in their entirety.

The present disclosure relates to an insulating layer for a multilayer printed circuit board, a multilayer printed circuit board including the same, and a method for fabricating the same. Specifically, the present disclosure relates to an insulating layer for a multilayer printed circuit board having excellent adhesion to a patterned metal layer, a multilayer printed circuit board including the same, and a method for fabricating the same.

2. Background of the Invention

Recent electronic devices have gradually become smaller in size, more lightweight, and highly functional. In order to satisfy such recent demand in the field of electronic devices, a semiconductor element has been required to be mounted inside the electronic device. In recent years, such a trend has been realized as semiconductor elements have become smaller in size and the integration density thereof has increased.

In order for a semiconductor element to receive an electrical signal in an electronic device, electrical wiring is essential, and in this case, insulation of the semiconductor element and the electrical wiring is required for stable electrical signal transmission.

In this way, a build-up semiconductor packaging process is used not only for electrical wiring connection between semiconductor elements and also for the formation of an insulating layer between these elements. Such a semiconductor packaging process has advantages in that it may improve the integration density of functional elements, allow electronic devices to become smaller in size, more lightweight and highly functional, achieve structural integration of electric functions, and reduce the assembly time period and costs.

In the build-up semiconductor packaging process, in order to form a microcircuit on the insulating layer, it is important to ensure adhesion between a build-up insulating layer and a conductive layer on which the circuit is formed. In recent years, due to a limit to an insulating layer pattern that may be formed by laser drilling, a method of forming a fine pattern by development with a weak alkali solution has been used.

Accordingly, the structure of melamine is known to be effective for improving adhesion and is widely used. However, melamine is insoluble in most solvents due to the highly stable structure thereof, and thus it is not well dispersed or dissolved and is not easily developed with a weak alkali solution. For this reason, melamine is difficult to use in the fabrication of fine patterns.

BRIEF SUMMARY OF THE INVENTION

The present disclosure to provide an insulating layer for a multilayer printed circuit board having excellent adhesion to a patterned metal layer, a multilayer printed circuit board including the same, and a method for fabricating the same.

In accordance with one aspect of the present disclosure, there is provided an insulating layer for a multilayer printed circuit board, the insulating layer including a patterned polymer resin layer containing an alkali-soluble resin, a thermosetting binder, and a melamine derivative, wherein the melamine derivative has a structure of the following Chemical Formula 1:

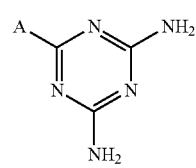

[Chemical Formula 1]

wherein A is an alkyl group containing 1 to 6 carboxyl groups, or an amine group containing 1 to 6 carboxyl groups.

In accordance with another aspect of the present disclosure, there is provided a multilayer printed circuit board including: the insulating layer; and a patterned metal layer positioned on the insulating layer.

In accordance with still another aspect of the present disclosure, there is provided a method for fabricating the insulating layer, the method including steps of: forming, on a substrate, a polymer resin layer containing an alkali-soluble resin, a thermosetting binder and a melamine derivative; forming a patterned layer on the polymer resin layer; developing and curing the polymer resin layer having the patterned layer formed thereon; and forming a patterned polymer resin layer by removing the patterned layer from the cured polymer resin layer, wherein the melamine derivative has a structure of the following Chemical Formula 1:

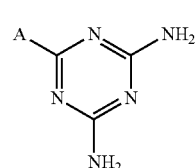

[Chemical Formula 1]

wherein A is an alkyl group containing 1 to 6 carboxyl groups, or an amine group containing 1 to 6 carboxyl groups.

The insulating layer for a multilayer printed circuit board according to one embodiment of the present disclosure has excellent adhesion to the patterned metal layer by containing the melamine derivative.

The multilayer printed circuit board according to another embodiment of the present disclosure has excellent adhesion between the insulating layer containing the melamine derivative and the patterned metal layer.

The insulating layer fabricated according to the insulating layer fabrication method according to still another embodiment of the present disclosure has excellent adhesion to the patterned metal layer by containing the melamine derivative.

DETAILED DESCRIPTION OF THE INVENTION

Figure 1A:
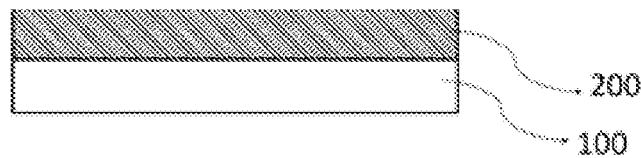
FIGS. 1A, 1B, 1C-1, 1C-2 and 1D are each a schematic view showing a method for fabricating an insulating layer according to one embodiment of the present disclosure.
Figure 1B:
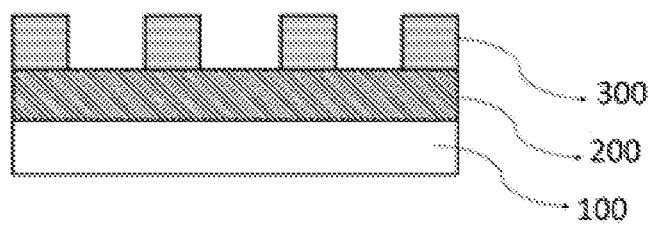

Throughout the present specification, it is to be understood that when any part is referred to as "including" any component, it does not exclude other components, but may further include other components, unless otherwise specified.

Throughout the present specification, when any member is referred to as being "on" another member, it not only refers to a case where any member is in contact with another member, but also a case where a third member exists between the two members.

Hereinafter, the present disclosure will be described in more detail.

An insulating layer for a multilayer printed circuit board according to one embodiment of the present disclosure includes a patterned polymer resin layer containing an alkali-soluble resin, a thermosetting binder, and a melamine derivative, wherein the melamine derivative has a structure of the following Chemical Formula 1:

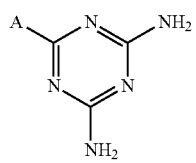

[Chemical Formula 1]

wherein A is an alkyl group containing 1 to 6 carboxyl groups, or an amine group containing 1 to 6 carboxyl groups.

Hereinafter, each component will be described in detail.

Alkali-Soluble Resin

According to one embodiment of the present disclosure, the patterned polymer resin layer contains an alkali-soluble resin.

According to one embodiment of the present disclosure, the alkali-soluble resin may include: one or more acidic functional groups; and one or more cyclic imide functional groups substituted with one or more amino groups. Examples of the acidic functional group are not particularly limited, but may include a carboxyl group or a phenol group. The alkali-soluble resin may include at least two acidic functional groups, so that the polymer resin layer may exhibit higher alkali developability and the developing rate of the polymer resin layer may be controlled.

The cyclic imide functional group substituted with an amino group may contain at least two amino groups and cyclic imide groups in the structure of the functional group. As the alkali-soluble resin contains at least two cyclic imide functional groups substituted with an amino group, the alkali-soluble resin may have a structure in which a large number of active hydrogen atoms are present in the amino group exist, and thus the reactivity thereof with the thermosetting binder during thermal curing may be improved, and at the same time, the curing density may be increased, thus increasing heat resistance reliability and mechanical properties.

In addition, as the plurality of cyclic imide functional groups are present in the alkali-soluble resin, the polarity thereof may be increased by the carbonyl group and tertiary amine group contained in the cyclic imide functional group, thus increasing the interfacial adhesion of the alkali-soluble resin. Accordingly, the polymer resin layer containing the alkali-soluble resin may have increased interfacial adhesion with the metal layer laminated thereon. Specifically, the polymer resin layer may have higher adhesion than the interfacial adhesion between a carrier film laminated on the metal layer and the metal layer, and thus as will be described later, physical separation between the carrier film and the metal layer may be possible.

More specifically, the cyclic imide functional group substituted with an amino group may include a functional group represented by the following Formula 1:

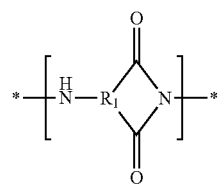

[Formula 1]

wherein $R_1$ is an alkylene group or alkenyl group having 1 to 10 carbon atoms, or 1 to 5 carbon atoms, or 1 to 3 carbon atoms, and "*" represents a bonding point. The alkylene group is a bivalent functional group derived from an alkane, and examples thereof include linear, branched or cyclic groups, such as a methylene group, an ethylene group, a propylene group, an isobutylene group, a sec-butylene group, a tert-butylene group, a pentylene group, a hexylene group, and the like. One or more hydrogen atoms contained in the alkylene group may be substituted with another substituent, and examples of the substituent include an alkyl group having 1 to 10 carbon atoms, an alkenyl group having 2 to 10 carbon atoms, an alkynyl group having 2 to 10 carbon atoms, an aryl group having 6 to 12 carbon atoms, a heteroaryl group having 2 to 12 carbon atoms, an arylalkyl group having 6 to 12 carbon atoms, a halogen atom, a cyano group, an amino group, an amidino group, a nitro group, an amide group, a carbonyl group, a hydroxyl group, a sulfonyl group, a carbamate group, an alkoxy group having 1 to 10 carbon atoms, and the like.

The term "substituted" as used herein means that another functional group is bonded instead of a hydrogen atom in the compound, and the position to be substituted is not limited as long as it is a position at which a hydrogen atom is substituted, that is, a position at which a hydrogen atom may be substituted with a substituent. When two or more hydrogen atoms are substituted, the two or more substituents may be the same as or different from each other.

The alkenyl group means that the above-mentioned alkylene group contains at least one carbon-carbon double bond in the middle or end thereof, and examples thereof include ethylene, propylene, butylene, hexylene, acetylene, and the like. One or more hydrogen atoms in the alkenyl group may be substituted with a substituent(s) in the same manner as in the alkylene group.

Preferably, the cyclic imide functional group substituted with an amino group may be a functional group represented by the following Formula 2:

[Formula 2]

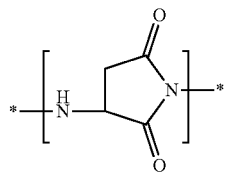

wherein "*" represents a bonding point.

As described above, the alkali-soluble resin includes a cyclic imide functional group, substituted with an amino group, together with an acidic functional group. Specifically, an acidic functional group may be bonded to at least one terminal of the cyclic imide functional group substituted with an amino group. In this case, the cyclic imide functional group substituted with an amino group and the acidic functional group may be bonded to each other via a substituted or unsubstituted alkylene group or a substituted or unsubstituted arylene group. For example, an acidic functional group may be bonded, via a substituted or unsubstituted alkylene group or a substituted or unsubstituted arylene group, to the terminal of the amino group contained in the cyclic imide functional group substituted with an amino group. An acidic functional group may be bonded, via a substituted or unsubstituted alkylene group or a substituted or unsubstituted arylene group, to the terminal of the imide functional group contained in the cyclic imide functional group substituted with an amino group.

More specifically, the terminal of the amino group contained in the cyclic imide functional group substituted with an amino group may refer to a nitrogen atom contained in the amino group in Formula 1, and the terminal of the imide functional group contained in the cyclic imide functional group substituted with an amino group may refer to a nitrogen atom contained in the cyclic imide functional group in Formula 1.

The alkylene group is a bivalent functional group derived from an alkane, and examples thereof include linear, branched or cyclic groups, such as a methylene group, an ethylene group, a propylene group, an isobutylene group, a sec-butylene group, a tert-butylene group, a pentylene group, a hexylene group, and the like. One or more hydrogen atoms contained in the alkylene group may be substituted with another substituent, and examples of the substituent include an alkyl group having 1 to 10 carbon atoms, an alkenyl group having 2 to 10 carbon atoms, an alkynyl group having 2 to 10 carbon atoms, an aryl group having 6 to 12 carbon atoms, a heteroaryl group having 2 to 12 carbon atoms, an arylalkyl group having 6 to 12 carbon atoms, a halogen atom, a cyano group, an amino group, an amidino group, a nitro group, an amide group, a carbonyl group, a hydroxyl group, a sulfonyl group, a carbamate group, an alkoxy group having 1 to 10 carbon atoms, and the like.

The arylene group means a divalent functional group derived from an arene, and examples thereof include cyclic groups, such as a phenyl group, a naphthyl group, and the like. One or more hydrogen atoms contained in the arylene group may be substituted with another substituent, and examples of the substituent include an alkyl group having 1 to 10 carbon atoms, an alkenyl group having 2 to 10 carbon atoms, an alkynyl group having 2 to 10 carbon atoms, an aryl group having 6 to 12 carbon atoms, a heteroaryl group having 2 to 12 carbon atoms, an arylalkyl group having 6 to 12 carbon atoms, a halogen atom, a cyano group, an amino group, an amidino group, a nitro group, an amide group, a carbonyl group, a hydroxyl group, a sulfonyl group, a carbamate group, an alkoxy group having 1 to 10 carbon atoms, and the like.

Examples of the method for producing the alkali-soluble resin are not particularly limited, but the alkali-soluble resin may be produced, for example, by reaction between a cyclic unsaturated imide compound and an amine compound. In this case, at least one of the cyclic unsaturated imide compound and the amine compound may contain an acidic functional group substituted at its terminal. That is, the terminal of the cyclic unsaturated imide compound or the amine compound, or the terminals of both the two compounds may be substituted with an acidic functional group. Details of the acid functional group are as described above.

The cyclic imide compound is a compound containing the above-mentioned cyclic imide functional group, and the cyclic unsaturated imide compound refers to a compound containing at least one unsaturated bond, that is, a double bond or a triple bond, in the cyclic imide compound.

The alkali-soluble resin may be produced by reaction between an amino group contained in the amine compound and a double bond or triple bond contained in the cyclic unsaturated imide compound.

Examples of the weight ratio for reaction between the cyclic unsaturated imide compound and the amine compound are not particularly limited, but for example, the amine compound may be mixed and used for reaction in an amount of 10 to 80 parts by weight, or 30 to 60 parts by weight, based on 100 parts by weight of the cyclic unsaturated imide compound.

Examples of the cyclic unsaturated imide compound include N-substituted maleimide compounds. The term "N-substituted" means that a functional group instead of a hydrogen atom is bonded to a nitrogen atom contained in the maleimide compound. The N-substituted maleimide compounds may be classified, according to the number of N-substituted maleimide compounds, into a monofunctional N-substituted maleimide compound and a polyfunctional N-substituted maleimide compound.

The monofunctional N-substituted maleimide compound is a compound in which a nitrogen atom contained in one maleimide compound is substituted with a functional group, and the polyfunctional N-substituted maleimide compound is a compound in which a nitrogen atom contained in each of two or more maleimide compounds is bonded via a functional group.

In the monofunctional N-substituted maleimide compound, the functional group substituting the nitrogen atom contained in the maleimide compound may include, without limitation, various known aliphatic, alicyclic, or aromatic functional groups, and the functional group substituting the the nitrogen atom may also include a functional group in which an aliphatic, alicyclic or aromatic functional group is substituted with an acidic functional group. Details of the acid functional group are as described above.

Specific examples of the monofunctional N-substituted maleimide compound include o-methylphenyl maleimide, p-hydroxyphenyl maleimide, p-carboxyphenyl maleimide, dodecyl maleimide, or the like.

In the polyfunctional N-substituted maleimide compound, the functional group that mediates the bond between the nitrogen atoms contained in each of the two or more maleimide compounds may include, without limitation, various known aliphatic, alicyclic, or aromatic functional groups. In a specific example, a 4,4'-diphenylmethane functional group or the like may be used. The functional group substituting the nitrogen atom may include a functional group in which an aliphatic, alicyclic, or aromatic functional group is substituted with an acidic functional group. Details of the acidic functional group are as described above.

Specific examples of the polyfunctional N-substituted maleimide compound include 4,4'-diphenylmethane bismaleimide (BMI-1000, BMI-1100, etc., commercially available from Daiwakasei Industry Co., Ltd.), phenylmethane bismaleimide, m-phenylene methane bismaleimide, bisphenol A diphenyl ether bismaleimide, 3,3'-dimethyl-5,5'-diethyl-4,4'-diphenylmethane bismaleimide, 4-methyl-1,3-phenylene bismaleimide, 1,6'-bismaleimide-(2,2,4-trimethyl)hexane, and the like.

As the amine compound, it is possible to use a primary amine compound containing at least one amino group (—NH$_2$) in the molecular structure. More preferably, it is possible to use a carboxylic acid compound substituted with an amino group, a polyfunctional amine compound containing two or more amino groups, or a mixture thereof.

In the carboxylic acid compound substituted with an amino group, the carboxylic acid compound may be a compound containing a carboxylic acid (—COOH) functional group in the molecule, and it may include all of aliphatic, alicyclic, or aromatic carboxylic acids depending on the kind of hydrocarbon bonded to the carboxylic acid functional group. As a large number of carboxylic acid functional groups, which are acid functional groups, are contained in the alkali-soluble resin through the carboxylic acid compound substituted with the amino group, the developing property of the alkali-soluble resin may be improved.

The term "substituted" means that another functional group is bonded instead of a hydrogen atom in the compound, and the position at which the carboxylic acid compound is substituted with an amino group is not limited as long as it is a position at which a hydrogen atom may be substituted. The number of amino groups as substituents may be 1 or more.

Specific examples of the carboxylic acid compound substituted with an amino group include 20 kinds of α-amino acids known as proteinogenic amino acids, 4-aminobutanoic acid, 5-aminopentanoic acid, 6-aminohexanoic acid, 7-amino heptanoic acid, 8-aminooctanoic acid, 4-aminobenzoic acid, 4-aminophenylacetic acid, 4-aminocyclohexane carboxylic acid, and the like.

Furthermore, the polyfunctional amine compound containing two or more amino groups may be a compound containing two or more amino groups (—NH$_2$) in the molecule, and it may include all of aliphatic, alicyclic, or aromatic polyfunctional amines depending on the type of hydrocarbon bonded to the amino group. The flexibility, toughness, copper foil adhesion, etc. of the alkali-soluble resin may be improved through the polyfunctional amine compound containing two or more amino groups.

Specific examples of the polyfunctional amine compound containing two or more amino groups include 1,3-cyclohexanediamine, 1,4-cyclohexanediamine, 1,3-bis(aminomethyl)-cyclohexane, 1,4-bis(aminomethyl)-cyclohexane, bis(aminomethyl)-norbornene, octahydro-4,7-methanoindene-1(2),5(6)-dimethanamine, 4,4'-methylenebis(cyclohexylamine), 4,4'-methylenebis(2-methylcyclohexylamine), isophoronediamine, 1,3-phenylenediamine, 1,4-phenylenediamine, 2,5-dimethyl-1,4-phenylenediamine, 2,3,5,6-tetramethyl-1,4-phenylenediamine, 2,4,5,6-tetrafluoro-1,3-phenylenediamine, 2,3,5,6-tetrafluoro-1,4-phenylenediamine, 4,6-diaminoresorcinol, 2,5-diamino-1,4-benzenedithiol, 3-aminobenzylamine, 4-aminobenzylamine, m-xylenediamine, p-xylenediamine, 1,5-diaminonaphthalene, 2,7-diaminofluorene, 2,6-diaminoanthraquinone, m-tolidine, o-tolidine, 3,3',5,5'-tetramethylbenzidine (TMB), o-dianisidine, 4,4'-methylenebis(2-chloroaniline), 3,3'-diaminobenzidine, 2,2'-bis(trifluoromethyl)-benzidine, 4,4'-diaminooctafluorobiphenyl, 4,4'-diamino-p-terphenyl, 3,3'-diaminodiphenylmethane, 3,4'-diaminodiphenylmethane, 4,4'-diaminodiphenylmethane, 4,4'-diamino-3,3'-dimethyldiphenylmethane, 4,4'-methylenebis(2-ethyl-6-methylaniline), 4,4'-methylenebis(2,6-diethylaniline), 3,3'-diaminobenzophenone, 4,4'-diaminobenzophenone, 4,4'-ethylenedianiline, 4,4'-diamino-2,2'-dimethylbibenzyl, 2,2'-bis(3-amino-4-hydroxyphenyl)propane, 2,2'-bis(3-aminophenyl)-hexafluoropropane, 2,2'-bis(4-aminophenyl)-hexafluoropropane, 2,2'-bis(3-amino-4-methylphenyl)-hexafluoropropane, 2,2'-bis(3-amino-4-hydroxyphenyl)-hexafluoropropane, α,α'-bis(4-aminophenyl)-1,4-diisopropylbenzene, 1,3-bis-[2-(4-aminophenyl)-2-propyl]benzene, 1,1'-bis(4-aminophenyl)-cyclohexane, 9,9'-bis(4-aminophenyl)-fluorene, 9,9'-bis(4-amino-3-chlorophenyl)fluorene, 9,9'-bis(4-amino-3-fluorophenyl)fluorene, 9,9'-bis(4-amino-3-methylphenyl)fluorene, 3,4'-diaminodiphenyl ether, 4,4'-diaminodiphenyl ether, 1,3-bis(3-aminophenoxy)-benzene, 1,3-bis(4-aminophenoxy)-benzene, 1,4-bis(4-aminophenoxy)-benzene, 1,4-bis(4-amino-2-trifluoromethylphenoxy)-benzene, 4,4'-bis(4-aminophenoxy)-biphenyl, 2,2'-bis-[4-(4-aminophenoxy)-phenyl] propane, 2,2'-bis-[4-(4-aminophenoxy)-phenyl]hexafluoropropane, bis(2-aminophenyl)sulfide, bis(4-aminophenyl)sulfide, bis(3-aminophenyl)sulfone, bis(4-aminophenyl)sulfone, bis(3-amino-4-hydroxy)sulfone, bis[4-(3-aminophenoxy)-phenyl]sulfone, bis-[4-(4-aminophenoxy)-phenyl]sulfone, o-tolidine sulfone, 3,6-diaminocarbazole, 1,3,5-tris(4-aminophenyl)-benzene, 1,3-bis(3-aminopropyl)-tetramethyldisiloxane, 4,4'-diaminobenzanilide, 2-(3-aminophenyl)-5-aminobenzimidazole, 2-(4-aminophenyl)-5-aminobenzoxazole, 1-(4-aminophenyl)-2,3-dihydro-1,3,3-trimethyl-1H-inden-5-amine, 4,6-diaminoresorcinol, 2,3,5,6-pyridine tetraamine, polyfunctional amines containing siloxane structures (PAM-E, KF-8010, X-22-161A, X-22-161B, KF-8012, KF-8008, X-22-1660B-3 and X-22-9409, which are products of Shin-Etsu Silicone Co., Ltd.), a polyfunctional amine containing a siloxane structure (Dow Corning 3055 which is a product of Dow Corning), polyfunctional amines containing polyether structures (Huntsman and BASF), and the like.

Furthermore, the alkali-soluble resin may include at least one repeating unit represented by the following Formula 3 and at least one repeating unit represented by the following Formula 4:

[Formula 3]

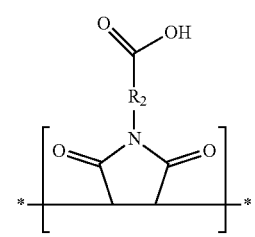

wherein $R_2$ is a direct bond, an alkylene group having 1 to 20 carbon atoms, an alkenyl group having 1 to 20 carbon atoms, or an arylene group having 6 to 20 carbon atoms, and "*" represents a bonding point,

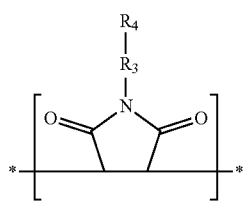

[Formula 4]

wherein $R_3$ is a direct bond, an alkylene group having 1 to 20 carbon atoms, an alkenyl group having 1 to 20 carbon atoms, or an arylene group having 6 to 20 carbon atoms, $R_4$ is —H, —OH, —$NR_5R_6$, a halogen, or an alkyl group having 1 to 20 carbon atoms, $R_5$ and $R_6$ may be each independently hydrogen, an alkyl group having 1 to 20 carbon atoms, or an aryl group having 6 to 20 carbon atoms, and "*" represents a bonding point.

Preferably, in Formula 3, $R_2$ may be phenylene, and in Formula 4, $R_3$ may be phenylene and $R_4$ may be —OH.

Meanwhile, the alkali-soluble resin may further include a vinyl-based repeating unit, in addition to the repeating unit represented by Formula 3 and the repeating unit represented by Formula 4. The vinyl-based repeating unit is a repeating unit contained in a homopolymer of a vinyl-based monomer containing at least one vinyl group in the molecule, and examples of the vinyl-based monomer are not particularly limited, and include ethylene, propylene, isobutylene, butadiene, styrene, acrylic acid, methacrylic acid, maleic anhydride, maleimide, or the like.

The alkali-soluble resin containing at least one repeating unit represented by Formula 3 and at least one repeating unit represented by Formula 4 may be produced by reaction between a polymer containing a repeating unit represented by the following Formula 5, an amine represented by the following Formula 6, and an amine represented by the following Formula 7:

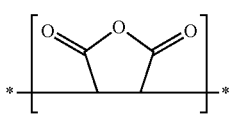

[Formula 5]

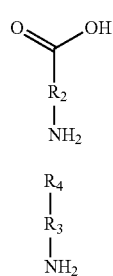

[Formula 6]

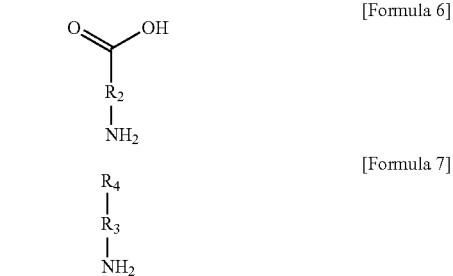

[Formula 7]

In Formulas 5 to 7, $R_2$ to $R_4$ are as defined above with respect to Formulas 3 and 4, and "*" represents a bonding point.

Specific examples of polymers containing the repeating unit represented by Formula 5 are not particularly limited, and include SMA (Cray Valley), Xiran (Polyscope), Scripset (Solenis), Isobam (Kuraray), Polyanhydride resin (Chevron Phillips Chemical Company), Maldene (Lindau Chemicals), and the like.

Furthermore, the alkali-soluble resin containing at least one repeating unit represented by Formula 3 and at least one repeating unit represented by Formula 4 may be produced by reaction between a compound represented by the following Formula 8 and a compound represented by the following Formula 9:

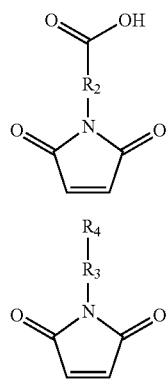

[Formula 8]

[Formula 9]

In Formulas 8 and 9, $R_2$ to $R_4$ are as defined above with respect to Formulas 3 and 4.

In addition, as the alkali-soluble resin, a well-known and commonly used carboxyl group-containing resin or phenol group-containing resin containing a carboxyl group or a phenol group in its molecule may be used. Preferably, the carboxyl group-containing resin or a mixture of the carboxyl group-containing resin and the phenol group-containing resin may be used.

The carboxyl group-containing resin may be any one of resins listed in (1) to (7) below, but is not limited thereto:

(1) a carboxyl group-containing resin obtained by reacting a polyfunctional epoxy resin with a saturated or unsaturated monocarboxylic acid followed by reacting with a polybasic acid anhydride, (2) a carboxyl group-containing resin obtained by reacting a bifunctional epoxy resin with a bifunctional phenol and/or a dicarboxylic acid followed by reacting with a polybasic acid anhydride, (3) a carboxyl group-containing resin obtained by reacting a polyfunctional phenolic resin with a compound having one epoxy group in its molecule followed by reacting with a polybasic acid anhydride, (4) a carboxyl group-containing resin obtained by reacting of a compound having two or more alcoholic hydroxyl groups in its molecule with a polybasic acid anhydride, (5) a polyamic acid resin obtained by reacting diamine with dianhydride or a copolymer resin of the polyamic acid resin, (6) a polyacrylic acid resin obtained by reacting an acrylic acid or a copolymer of the polyacrylic acid resin, and (7) a resin produced by ring-opening a polymaleic anhydride resin (obtained by reacting maleic anhydride) and an anhydride of a copolymer of the polymaleic anhydride resin with a weak acid, a diamine, an imidazole, or dimethyl sulfoxide.

More specific examples of the carboxyl group-containing resin include CCR-1291H (Nippon Kayaku), SHA- 1216CA60 (Shin-A T&C), Noverite K-700 (Lubrizol), or a mixture of two or more thereof.

Examples of the phenolic group-containing resin are not particularly limited, but include novolac resins such as phenol novolac resin, cresol novolac resin, bisphenol F (BPF) novolac resin, or bisphenol A based resins such as 4,4'-(1-(4-(2-(4-hydroxyphenyl)propan-2-yl)phenyl)ethane-1,1-diyl)diphenol, which may be used alone or in combination.

The alkali-soluble resin may have an acid value of 50 mgKOH/g to 250 mgKOH/g, or 70 mgKOH/g to 200 mgKOH/g, as determined by KOH titration. Examples of the method of measuring the acid value of the alkali-soluble resin are not particularly limited, but the following method may be used, for example. A KOH solution (solvent: methanol) having a concentration of 0.1 N was prepared as a base solution, and alpha-naphtholbenzein (pH: 0.8 to 8.2 yellow, or 10.0 blue green) was prepared as an indicator. Subsequently, about 1 g to 2 g of the alkali-soluble resin was sampled and dissolved in 50 g of a dimethylformaldehyde (DMF) solvent, and then the indicator was added thereto, followed by titration with the base solution. At the time of completion of the titration, the acid value was determined in units of mg KOH/g based on the amount of base solution used.

If the acid value of the alkali-soluble resin excessively decreases to less than 50 mgKOH/g, the developing property of the alkali-soluble resin may be lowered, thus making it difficult to perform the development process. In addition, if the acid value of the alkali-soluble resin excessively increases to more than 250 mgKOH/g, phase separation from other resins may occur due to increased polarity.

Thermosetting Binder

According to one embodiment of the present disclosure, the patterned polymer resin layer contains a thermosetting binder.

The thermosetting binder may include an epoxy group and at least one functional group selected from the group consisting of an oxetanyl group, a cyclic ether group, a cyclic thioether group, a cyanide group, a maleimide group and a benzoxazine group, which are heat-curable functional groups. That is, the thermosetting binder necessarily includes an epoxy group, may include, in addition to the epoxy group, an oxetanyl group, a cyclic ether group, a cyclic thioether group, a cyanide group, a maleimide group, a benzoxazine group, or a mixture of two or more thereof.

This thermosetting binder can ensure the heat resistance or mechanical properties of the insulating layer by forming a crosslink with the alkali-soluble resin or the like through heat curing.

More specifically, as the thermosetting binder, it is possible to use a polyfunctional resin compound containing the above-described two or more functional groups in its molecule.

The polyfunctional resin compound may include a resin containing two or more cyclic ether groups and/or cyclic thioether groups (hereinafter referred to as cyclic (thio)ether groups) in its molecule.

The thermosetting binder containing two or more cyclic (thio)ether groups in its molecule may include a compound having at least two 3-, 4- or 5-membered cyclic ether groups and/or at least two cyclic thioether groups in its molecule.

Examples of the compound having two or more cyclic thioether groups in the molecule include bisphenol A episulfide resin YL7000 manufactured by Japan Epoxy Resin, and the like.

In addition, the polyfunctional resin compound may include a polyfunctional epoxy compound containing at least two epoxy groups in its molecule, a polyfunctional oxetane compound containing at least two oxetanyl groups in its molecule, a episulfide resin containing two or more thioether groups in its molecule, a polyfunctional cyanate ester compound containing at least two cyanide groups in its molecule, or a polyfunctional benzoxazine compound containing at least two benzoxazine groups in its molecule.

Specific examples of the polyfunctional epoxy compound include bisphenol A-type epoxy resin, hydrogenated bisphenol A-type epoxy resin, brominated bisphenol A-type epoxy resin, bisphenol F-type epoxy resin, bisphenol S-type epoxy resin, novolac-type epoxy resin, phenol novolac-type epoxy resin, cresol novolac-type epoxy resin, N-glycidyl-type epoxy resin, bisphenol A novolac-type epoxy resin, bixylenol-type epoxy resin, biphenol-type epoxy resin, chelate-type epoxy resin, glyoxal-type epoxy resin, amino group-containing epoxy resin, rubber-modified epoxy resin, dicyclopentadiene phenolic-type epoxy resin, diglycidylphthalate resin, heterocyclic epoxy resin, tetraglycidyl xylenoylethane resin, silicone-modified epoxy resin, E-caprolactone-modified epoxy resin, and the like. In addition, in order to impart flame retardancy, it is possible to use those in which an atom such as phosphorus is introduced into the structure. When these epoxy resins are heat-cured, they improve the properties of the cured coating layer, such as adhesion, solder heat resistance, and electroless plating resistance.

Examples of the polyfunctional oxetane compound include polyfunctional oxetanes such as bis[(3-methyl-3-oxetanylmethoxy)methyl]ether, bis[(3-ethyl-3-oxetanylmethoxy)methyl]ether, 1,4-bis[(3-methyl-3-oxetanylmethoxy)methyl]benzene, 1,4-bis[(3-ethyl-3-oxetanylmethoxy)methyl]benzene, (3-methyl-3-oxetanyl)methylacrylate, (3-ethyl-3-oxetanyl)methylacrylate, (3-methyl-3-oxetanyl)methylmethacrylate, (3-ethyl-3-oxetanyl)methylmethacrylate, or oligomers or copolymers thereof, as well as etherification products of oxetane alcohol with a hydroxyl group-containing resin such as novolac resin, poly(p-hydroxystyrene), cardo bisphenol, calixarene, calixresorcin arene or silsesquioxane; and the like. Other examples include copolymers of a unsaturated monomer having an oxetane ring with an alkyl (meth)acrylate.

Examples of the polyfunctional cyanate ester compound include bisphenol A-type cyanate ester resin, bisphenol E-type cyanate ester resin, bisphenol F-type cyanate ester resin, bisphenol S-type cyanate ester resin, bisphenol M-type cyanate ester resin, novolac-type cyanate ester resin, phenol novolac-type cyanate ester resin, cresol novolac type cyanate ester resin, bisphenol A novolac-type cyanate ester resin, biphenol-type cyanate ester resin, or oligomers or copolymers thereof.

Examples of the polyfunctional maleimide compound include 4,4'-diphenylmethanebismaleimide, phenylnnethane bismaleimide, m-phenylmethane bismaleimide, bisphenol A diphenyl ether bismaleimide, 3,3'-dimethyl-5,5'-diethyl-4,4'-diphenylmethane bismaleimide, 4-methyl-1,3-phenylenebismaleimide, 1,6'-bismaleimide-(2,2,4-trimethyl)hexane, and the like.

Examples of the polyfunctional benzoxazine compound include bisphenol A-type benzoxazine resin, bisphenol F-type benzoxazine resin, phenolphthalein-type benzoxazine resin, thiodiphenol-type benzoxazine resin, dicyclopentadiene-type benzoxazine resin, 3,3'-(methylene-1,4-diphenylene)bis(3,4-dihydro-2H-1,3-benzoxazine) resin, and the like.

More specific examples of the multifunctional resin compound include YDCN-500-80P (Kukdo Chemical Co., Ltd.), phenol novolac-type cyanate ester resin PT-30S (LONZA Ltd.), phenylmethane-type maleimide resin BMI-2300 (Daiwa Kasei Kogyo Co., Ltd.), P-d type benzoxazine resin (Shikoku Chemicals Corporation), and the like.

The polymer resin layer may contain the thermosetting binder in an amount of 1 to 150 parts by weight, or 10 to 100 parts by weight, or 20 to 50 parts by weight, based on 100 parts by weight of the alkali-soluble resin. If the content of the thermosetting binder is excessively high, the developing property of the polymer resin layer may decrease and the strength of the polymer resin layer may decrease. On the other hand, if the content of the thermosetting binder is excessively low, not only the polymer resin layer may be excessively developed, but also the uniformity during coating may deteriorate.

Melamine Derivative

According to one embodiment of the present disclosure, the patterned polymer resin layer contains a melamine derivative. The melamine derivative has excellent compatibility while improving adhesion between an insulating layer and a patterned metal layer to be formed later formed on the insulating layer. Thus, the melamine derivative makes it easy to prepare a polymer resin composition.

According to one embodiment of the present disclosure, the melamine derivative has a structure of the following Chemical Formula 1. Therefore, the melamine derivative contains in its molecule 1 to 6 carboxyl groups which are acidic functional groups having relatively high reactivity, and thus may actively react with the thermosetting binder. As a result, the melamine derivative may further increase the adhesion between the insulating layer and the patterned metal layer. In addition, the melamine derivative may be easily developed even with weak alkali solution, and thus may be useful for the formation of the insulating layer.

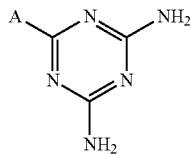

[Chemical Formula 1]

In Chemical Formula 1 above, A is either an alkyl group containing 1 to 6, 1 to 5, 2 to 6, 1 to 4, 2 to 5, 3 to 6, 1 to 3, 2 to 4, 3 to 5 or 4 to 6 carboxyl groups, or an amine group containing 1 to 6, 1 to 5, 2 to 6, 1 to 4, 2 to 5, 3 to 6, 1 to 3, 2 to 4, 3 to 5, or 4 to 6 carboxyl groups. The melamine derivative may be produced by various methods, and the method for producing the melamine derivative is not limited as long as the melamine derivative has the structure of Chemical Formula 1.

In Chemical Formula 1, A may contain 1 to 4 or 1 to 2 sulfur atoms.

According to one embodiment of the present disclosure, the polymer resin layer may contain the melamine derivative in an amount of 3 to 30 parts by weight or 10 to 30 parts by weight based on 100 parts by weight of the alkali-soluble resin. When the melamine derivative is contained in an amount within the above range, the insulating layer may have excellent adhesion to the patterned metal layer.

According to one embodiment of the present disclosure, the melamine derivative may have a solubility of 5 to 20 in an aprotic solvent at 25° C. The aprotic solvent may be one or more of dimethyl sulfoxide, N-methyl pyrrolidone, dimethylacetamide, and dimethylformamide. The "solubility" may mean the mass (g) of the melamine derivative that may be maximally dissolved in 100 g of a solvent. That is, for example, 10 to 20 g of the melamine derivative may be dissolved in 100 g of dimethyl sulfoxide.

Multilayer Printed Circuit Board

A multilayer printed circuit board according to another embodiment of the present disclosure includes: the insulating layer; and a patterned metal layer positioned on the insulating layer.

In the multilayer printed circuit board according to one embodiment of the present disclosure, the patterned metal layer may have a peel strength of 0.4 kgf/cm to 1.2 kgf/cm, 0.5 kgf/cm to 1.0 kgf/cm, 0.5 kgf/cm to 0.7 kgf/cm, or 0.51 kgf/cm to 0.54 kgf/cm, as measured according to the IPC-TM-650 standard after the multilayer printed circuit board is left to stand at a temperature of 135° C. and a humidity of 85% for 48 hours. When the patterned metal layer has a peel strength within the above range, the insulating layer may have excellent metal adhesion.

As the insulating layer fabricated by the method according to one embodiment of the present disclosure contains the melamine derivative having the structure of Chemical Formula 1, the insulating layer may have excellent adhesion to the patterned metal layer formed on the insulating layer.

Method for Fabricating Insulating Layer

The present disclosure also provides a method for fabricating the insulating layer, the method including steps of: forming, on a substrate, a polymer resin layer containing an alkali-soluble resin, a thermosetting binder and a melamine derivative; forming a patterned layer on the polymer resin layer; developing and curing the polymer resin layer having the patterned layer formed thereon; and forming a patterned polymer resin layer by removing the patterned layer from the cured polymer resin layer, wherein the melamine derivative has the structure of Chemical Formula 1.

Figures 1, 1C:
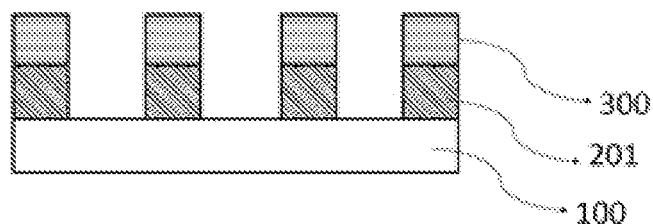
Figures 1, 1C, 2:
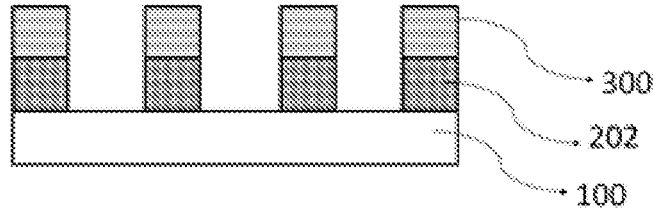
Figure 1D:
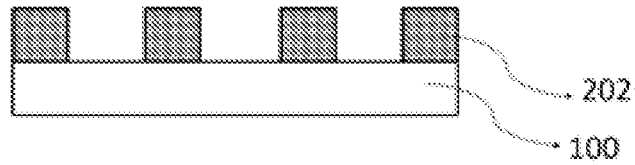

FIG. 1 is a schematic view showing a method for fabricating an insulating layer according to one embodiment of the present disclosure. Referring to FIG. 1, the method for fabricating an insulating layer according to one embodiment of the present disclosure includes steps of: (A) forming a polymer resin layer 200 on a substrate 100; (B) forming a patterned layer 300 on the polymer resin layer 200; (C-1) developing the polymer resin layer 200, and (C-2) curing the developed polymer resin layer; and (D) removing the patterned layer 300.

Hereinafter, each step will be described in detail.

(1) Step of Forming, on Substrate, Polymer Resin Layer Containing Alkali-Soluble Resin, Thermosetting Binder and Melamine Derivative According to one embodiment of the present disclosure, a polymer resin layer that serves as a base for the insulating layer is first formed on a substrate.

The substrate may be a circuit board such as a copper clad laminate, a sheet, a multilayer printed circuit board, or a semiconductor material such as a silicon wafer. The thickness of the polymer resin layer may be 1 µm to 500 µm, or 3 µm to 500 µm, or 3 µm to 200 µm, or 1 µm to 60 µm, or 5 µm to 30 µm.

The polymer resin layer may contain an alkali-soluble resin, a thermosetting binder and a melamine derivative. Specifically, after a polymer resin composition containing the alkali-soluble resin, the thermosetting binder and the melamine derivative having the structure of Chemical Formula 1 is prepared, the polymer resin layer may be formed using the same.

Details of the polymer resin composition containing the alkali-soluble resin, the thermosetting binder and the melamine derivative having the structure of Chemical Formula 1 are as described above.

A method of forming the polymer resin layer is not limited. However, for example, the polymer resin layer may be formed using a method in which the polymer resin composition is applied directly onto a substrate and dried or cured, or a method in which the polymer resin composition is applied onto a separate carrier film and dried or cured, and the carrier film having the polymer resin composition applied thereto is laminated onto a substrate and then removed. Preferably, it is possible to use a method in which an adhesive layer is formed on the substrate, and then the adhesive layer is coated directly with the polymer resin composition, or a method in which the polymer resin composition is applied onto a carrier film to form the polymer resin layer, and then the polymer resin layer and an adhesive layer on a substrate are laminated together, or a method in which the polymer resin composition is applied onto a carrier film to form the polymer resin layer, and then an adhesive layer is formed on the polymer resin layer, and a substrate and the adhesive layer are laminated together.

Examples of the adhesive layer are not particularly limited, and various adhesive layers widely known in the fields of semiconductor elements and electric and electronic materials may be used without limitation. For example, a debondable temporary adhesive or a die attach film (DAF) may be used.

(2) Step of Forming Patterned Layer on Polymer Resin Layer

According to one embodiment of the present disclosure, a patterned layer is formed on the polymer resin layer formed on the substrate.

As used herein, the term "patterned layer" refers to a layer that is positioned on the polymer resin layer such that a portion of the polymer resin layer is exposed and the other portion of the polymer resin layer is not exposed, whereby a pattern may be formed on the polymer resin layer by developing the exposed portion. That is, the patterned layer functions as a resist mask that exposes a portion of the polymer resin layer such that the portion may be developed, and protects the other portion of the polymer resin layer from development such that the pattern of the patterned layer may be completely transferred onto the polymer resin layer.

A method of forming the patterned layer is not particularly limited. For example, the patterned layer may be formed using a photosensitive resin layer.

The step of forming the patterned layer on the polymer resin layer may include steps of: forming a photosensitive resin layer on the polymer resin layer; and exposing the photosensitive resin layer, and alkali-developing an unexposed portion of the photosensitive resin layer to form the patterned layer.

Examples of a method of forming the photosensitive resin layer on the polymer resin layer are not particularly limited. However, for example, it is possible to use a method in which a film-type photosensitive resin such as a photosensitive dry film resist is laminated onto the polymer resin layer, or a method in which the polymer resin layer is coated with a photosensitive resin composition by a spray or dipping method and the coated composition is pressed.

The photosensitive resin layer contains a polymer whose molecular structure and physical properties are changed by the action of light. As the photosensitive resin layer, a photosensitive dry film resist (DFR) or a photosensitive liquid resist may be used. The photosensitive resin layer may exhibit photosensitivity and alkali solubility. Accordingly, the molecular structure of the photosensitive resin layer may be changed by an exposure process of irradiating the photosensitive resin layer with light, and the photosensitive resin layer may be etched or removed by a developing process of bringing an alkaline developer into contact with the same.

Accordingly, when a portion of the photosensitive resin layer is selectively exposed and then alkali development is performed, the exposed portion is not developed, and only the unexposed portion may be selectively etched and removed. As such, a portion of the photosensitive resin layer, which remains intact without being alkali developed after exposure, may be the patterned layer.

That is, examples of a method of selectively exposing the photosensitive resin layer include a method in which a photomask formed to have a predetermined pattern is brought into contact with the photosensitive resin layer and the photosensitive resin layer is irradiated with UV light, or a method in which a predetermined pattern included in a mask is imaged on the photosensitive resin layer through a projection objective lens, followed by irradiation with UV light, or a method in which the photosensitive resin layer is directly imaged using a laser diode as a light source, and then irradiated with UV light. In this case, the photosensitive resin layer may be irradiated with UV light at a dose of 5 $mJ/cm^2$ to 600 $mJ/cm^2$.

In addition, examples of a method of alkali-developing the photosensitive resin layer after exposure include a method of treating the photosensitive resin layer with an alkali developer. Examples of the alkali developer are not particularly limited. However, for example, an aqueous solution of an alkali such as potassium hydroxide, sodium hydroxide, sodium carbonate, potassium carbonate, sodium phosphate, sodium silicate, ammonia, tetramethylammonium hydroxide, or amine, may be used at an adjusted concentration and temperature. In addition, a commercially available alkali developer may be used. Although the specific amount of alkali developer used is not particularly limited, it is necessary to adjust the concentration and temperature of the alkali developer so as not to cause damage to the patterned layer. For example, a 0.5 to 3% aqueous solution of sodium carbonate at a temperature of 25 to 35° C. may be used.

The thickness of the patterned layer formed on the polymer resin layer may be 1 µm to 500 µm, or 3 µm to 500 µm, or 3 µm to 200 µm, or 1 µm to 60 µm, or 5 µm to 30 µm.

If the thickness of the patterned layer excessively increases, the resolution of the polymer resin layer may decrease.

(3) Step of Developing and Curing Polymer Resin Layer

According to one embodiment of the present disclosure, the polymer resin layer having the patterned layer formed thereon is developed and cured. Specifically, the polymer resin layer, a portion of which has been exposed through the patterned layer, is developed to form a pattern on the polymer resin layer, and then the polymer resin layer is heat-cured or photocured.

That is, in the step of developing the polymer resin layer exposed through the patterned layer, the patterned layer remains intact and serves as a resist mask because the patterned layer is not removed by a developer. In addition, the alkali developer may come into contact with the patterned layer and the underlying polymer resin layer through an opening of the patterned layer. At this time, a portion of the polymer resin layer, with which the developer comes into contact, may be dissolved and removed, because the polymer resin layer has alkali solubility (which means that the polymer resin layer is dissolved by the alkali developer) by containing the alkali-soluble resin.

Thus, the polymer resin layer exposed through the patterned layer means a polymer resin layer portion whose surface does not contact the patterned layer. The step of alkali-developing the polymer resin layer exposed through the patterned layer may include a step of allowing the alkali developer to pass through the patterned layer and contact the underlying polymer resin layer.

Through the step of developing the polymer resin layer, the polymer resin layer may be patterned to have the same shape as the pattern of the patterned layer.

After the polymer resin layer is developed as described above, it may be cured. Specifically, the polymer resin layer may be heat-cured or photocured. As the step of curing the polymer resin layer is included, it is possible to minimize damage to the polymer resin layer during subsequent removal of the patterned layer.

Through the step of curing the polymer resin layer, a main chain containing an ester bond may be formed in the polymer resin block. Examples of a method of forming the ester bond include a method of photo-curing the polymer resin layer through an acrylic resin in which acrylic acid is ester-bonded, or a method of heat-curing the polymer resin layer such that an ester bond is formed by reaction between carboxylic acid and epoxy.

In this case, specific conditions for heat-curing are not limited, and may be adjusted to preferable conditions depending on a method of removing the patterned layer. For example, when the patterned layer is to be removed by treatment with a photoresist stripper solution, the step of heat-curing the polymer resin layer may be performed at a temperature of 60 to 150° C. for 5 minutes to 2 hours. If the heat-curing temperature of the polymer resin layer is excessively low or the heat-curing time thereof becomes shorter, the polymer resin layer may be damaged by the stripper solution. On the other hand, if the heat-curing temperature of the polymer resin layer is high or the heat-curing time thereof becomes longer, it may be difficult to remove the patterned layer by a stripper solution, excessive warpage may occur in the polymer resin layer.

As another example, when the patterned layer is to be removed through a desmear process, the step of heat-curing the polymer resin layer may be performed at a temperature of 150 to 230° C. for 1 hour to 4 hours.

(4) Step of Removing Patterned Layer

According to one embodiment of the present disclosure, a patterned polymer resin layer is formed by removing the patterned layer from the cured polymer resin layer.

For removal of the patterned layer, it is preferable to use a method capable of removing only the patterned layer without removing the underlying polymer resin layer as possible.

The removal of the patterned layer may be performed by treatment with a photoresist stripper solution.

Examples of a method of treating the patterned layer with the photoresist stripper solution are not particularly limited. However, for example, as the photoresist stripper solution, an aqueous solution of an alkali such as potassium hydroxide and sodium hydroxide, may be used at an adjusted concentration and temperature. In addition, it is also possible to use a commercially available product such as a Resistrip product group (commercially available from by Atotech), or ORC-731, ORC-723K, ORC-740, or SLF-6000 (commercially available from Orchem Corporation). The specific amount of photoresist stripper solution used is not particularly limited, but it is necessary to adjust the concentration and temperature of the photoresist stripper solution so as not to cause damage to the pattern of the underlying polymer resin layer. For example, a 1% to 5% aqueous solution of sodium hydroxide at 25° C. to 60° C. may be used.

Examples of a method of stripping the patterned layer using the desmear process are not particularly limited. For example, for stripping of the patterned layer, commercially available products may be used depending on each process condition, such as Sweller chemicals such as Securiganth E, Securiganth HP, Securiganth BLG, Securiganth MV SWELLER, or Securiganth SAP SWELLER, permanganate chemicals such as Securiganth P 500, Securiganth MV ETCH P, or Securiganth SAP ETCH P, or reducing agent chemicals such as Securiganth E Reduction Cleaner, Securiganth HP Reduction Cleaner, Securiganth BLG Reduction Cleaner, Securiganth MV Reduction Cleaner, or Securiganth SAP Reduction Cleaner, which are desmear process chemicals commercially available from Atotech; or Sweller chemicals such as ORC-310A, ORC-315A, ORC-315H or ORC-312, permanganate chemicals such as ORC-340B, or reducing agent chemicals such as ORC-370 or ORC-372, which are desmear process chemicals commercially available from Orchem Corporation.

According to an embodiment of the present disclosure, after the step of removing the patterned layer, a step of curing the patterned polymer resin layer may be further included.

If the above-described curing of the polymer resin layer is primary curing, secondary curing may be performed on the patterned polymer resin layer after the step of removing the patterned layer as described above. Thereby, the chemical resistance of the finally fabricated insulating layer may be improved.

Examples of a method for secondary curing are not particularly limited, and a heat-curing or photocuring method may be used without limitation. The secondary curing may be performed at a temperature of 150° C. to 250° C. for 0.1 hour to 10 hours.

According to one embodiment of the present disclosure, after forming the patterned polymer resin layer, a step of subjecting the patterned polymer resin layer to roughening treatment to improve adhesion to the patterned metal layer to be formed later may be further included.

The roughening treatment may be performed by a dry method or a wet method depending on conditions. Examples of the dry method include vacuum, atmospheric pressure or gas plasma treatment, gas excimer UV treatment, and the like, and examples of the wet method include desmear treatment.

Through this roughening treatment, it is possible to increase the surface roughness of the patterned polymer resin layer, thus increasing the adhesion thereof to a metal that is deposited on the patterned polymer resin layer.

Method for Fabricating Multiple Printed Circuit Board

A method of fabricating a multilayer printed circuit board according to another embodiment of the present disclosure includes steps of: fabricating an insulating layer by the method according to one embodiment of the present disclosure; and forming a patterned metal layer on the insulating layer.

The term "patterned metal layer" may refer to a metal pattern layer. The step of forming the patterned metal layer may include steps of: forming a metal thin film on the insulating layer; forming a patterned layer on the metal thin film; depositing a metal on the metal thin film exposed through the patterned layer; and removing the patterned layer, and removing the metal thin film exposed by removal of the patterned layer.

It has been found that, as the insulating layer fabricated by the method according to one embodiment of the present disclosure includes a predetermined opening pattern, the inside of the opening pattern may be filled with a metal in the process of newly laminating the patterned metal layer on the insulating layer, whereby metal substrates positioned on and under of the insulating layer may be connected together, thereby fabricating a multiple printed circuit board. Based on this finding, the present disclosure has been completed.

Before the step of forming the metal thin film, a step of forming a surface treatment layer on the insulating layer may be further included. Thereby, the adhesion between the patterned metal layer and the insulating layer may be further improved.

Specifically, as an example of a method of forming the surface treatment layer on the insulating layer, at least any one of an ion-assisted reaction method, an ion beam treatment method, and a plasma treatment method may be used. The plasma treatment method may include any one of an atmospheric pressure plasma treatment method, a DC plasma treatment method, and an RF plasma treatment method. As a result of the surface treatment process, a surface treatment layer containing a reactive functional group may be formed on the surface of the insulating layer. Another example of the method of forming the surface treatment layer on the insulating layer may include a method of depositing a chromium (Cr) or titanium (Ti) metal on the surface of the insulating layer to have a thickness of 50 nm to 300 nm.

In the step of forming the metal thin film on the insulating layer, examples of the method of forming the metal thin film include a dry deposition process or a wet deposition process. Specific examples of the dry deposition process include a vacuum deposition process, an ion plating process, a sputtering process, and the like.

Meanwhile, specific examples of the wet deposition process include electroless plating of various metals, and electroless copper plating is generally used.

In the step of forming the patterned layer on the metal thin film, details related to the formation of the patterned layer may include the details described above with respect to the embodiment.

In the step of depositing the metal on the metal thin film exposed through the patterned layer, the metal thin film exposed through the patterned layer means a portion of the metal thin film, the surface of which is not in contact with the patterned layer. As the metal to be deposited, copper may be used. Examples of a method of depositing the metal are not particularly limited, and various known physical or chemical vapor deposition methods may be used without limitation. As a general-purpose example, an electrolytic copper plating method may be used.

In the step of removing the patterned layer and removing the metal thin film exposed by removal of the patterned layer, the metal thin film exposed by removal of the patterned layer refers to a portion of the metal thin film, the surface of which was in contact with the patterned layer. Details related to removal of the patterned layer may include the details described above with respect to the embodiment.

The multilayer printed circuit board fabricated by the method for fabricating a multilayer printed circuit board may be used again as a build-up material. For example, a first process of forming an insulating layer on the multilayer printed circuit board according to the insulating layer fabrication method of the embodiment, and a second process of forming a metal substrate on the insulating layer according to the multilayer printed circuit board fabrication method of the another embodiment may be repeated.

Accordingly, the number of stacked layers included in the multilayer printed circuit board fabricated by the multilayer printed circuit board fabrication method is also not particularly limited, and the multilayer printed circuit board may have, for example, one or more layers or 1 to 20 layers depending on the intended use or purpose thereof.

Hereinafter, the present disclosure will be described in detail with reference to examples. However, the examples according to the present disclosure may be modified into various different forms, and the scope of the present disclosure is not interpreted as being limited to the examples described below. The examples of the present disclosure are provided to more completely explain the present disclosure to those skilled in the art.

Production Example 1

242 g of dimethyl sulfoxide as aprotic solvent, 105 g of thiomalic acid, 137 g of 2-vinyl-4,6-diamino-1,3,5-triazine, and 16 g of azobisisobutyronitrile were placed in a 1-L reactor, heated to 80° C. while being stirred, and then kept for 24 hours to obtain a transparent solution. The obtained solution was precipitated in methanol, and the formed solid was dried, thereby producing a melamine derivative of the following Chemical Formula 2:

[Chemical Formula 2]

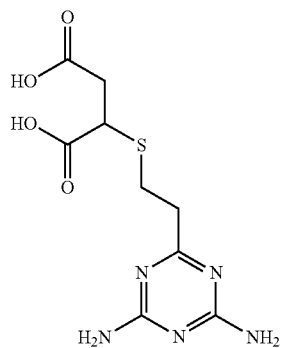

Production Example 2

205 g of dimethyl sulfoxide as aprotic solvent, 105 g of thiomalic acid, 100 g of diallylmelamine, and 16 g of azobisisobutyronitrile were placed in a 1-L reactor, heated to 80° C. while being stirred, and then kept for 24 hours to obtain a transparent solution. The obtained solution was precipitated in methanol, and the formed solid was dried, thereby producing a melamine derivative of the following Chemical Formula 3:

[Chemical Formula 3]

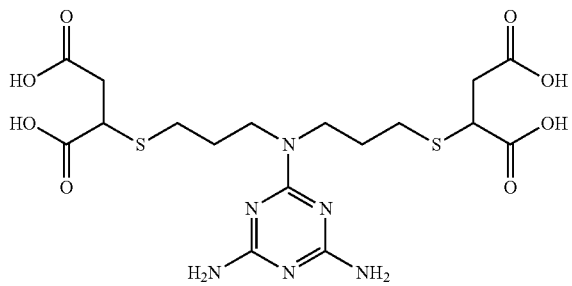

Production Example 3

221 g of a 10 wt % solution of sodium hydroxide, 75 g of glycine, and 146 g of 2-chloro-4,6-diamino-1,3,5-triazine were placed in a 1-L reactor, heated to 80° C. while being stirred, and then kept for 24 hours to obtain a transparent solution. The obtained solution was precipitated in methanol, and the formed solid was dried, thereby producing a melamine derivative of the following Chemical Formula 4:

[Chemical Formula 4]

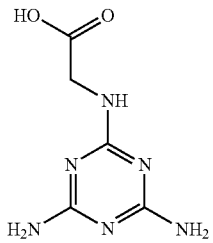

Production Example 4: Alkali-Soluble Resin 543 g of dimethylacetamide (DMAc) as a solvent, 350 g of SMA1000 (manufactured by Cray Valley), 144 g of 4-aminobenzoic acid (PABA), and 49 g of 4-aminophenol (PAP) were placed and mixed together in a 2-liter coolable and heatable reactor equipped with a thermometer, a stirrer, a reflux condenser and a quantitative moisture analyzer. After the temperature of the reactor was set to 80° C. under a nitrogen atmosphere, the acid anhydride and the aniline derivative were allowed to react continuously for 24 hours to form an amic acid. Then, the temperature of the reactor was set to 150° C., and the imidization reaction was performed continuously for 24 hours to produce an alkali-soluble resin solution having a solid content of 50%.

Fabrication of Insulating Layer

Example 1

As a substrate, a copper substrate having a size of 5 cm*5 cm was prepared. A mixture was prepared, including 100 parts by weight of the resin, synthesized in Production Example 4, as an alkali-soluble resin, 30 parts by weight of MY-510 (manufactured by Huntsman) as a thermosetting binder, 180 parts by weight of SC2050 MB as an inorganic filler, 4 parts by weight of the melamine derivative produced in Production Example 1, and 20 parts by weight of DMSO as a solvent. The mixture was applied onto a PET film and dried to fabricate a polymer resin layer having a thickness of 15 μm.

The fabricated polymer resin layer was vacuum-laminated at 85° C. onto a circuit board in which a copper line was formed on a copper clad laminate. Then, the PET film was removed. Photosensitive dry film resist KL1015 (manufactured by Kolon Industries) having a thickness of 15 μm was laminated onto the polymer resin layer at 110° C.

A circular negative photomask having a diameter of 30 μm was brought into contact with the surface of the photosensitive dry film resist, the photosensitive dry film resist was irradiated with UV light (dose of 25 mJ/cm$^2$), and then the dry film resist and the polymer resin layer were sequentially developed with a 1% sodium carbonate developer solution at 30° C. At this time, the photosensitive dry film resist having a pattern formed therein acted as a protective layer for the polymer resin layer, and thus the same pattern as that of the photosensitive dry film resist was also formed in the polymer resin layer. Subsequently, the polymer resin layer was heat-cured at a temperature of 100° C. for 1 hour, and then the residue and the photosensitive dry film resist were removed using a 3% sodium hydroxide resist stripper solution at a temperature of 50° C. Then, the polymer resin layer was heat-cured at a temperature of 200° C. for 1 hour, thereby fabricating an insulating layer.

Example 2

An insulating layer was fabricated in the same manner as in Example 1, except that 4 parts by weight of the melamine derivative produced in Production Example 2 was used instead of the melamine derivative produced in Production Example 1.

Example 3

An insulating layer was fabricated in the same manner as in Example 1, except that 4 parts by weight of the melamine derivative produced in Production Example 3 was used instead of the melamine derivative produced in Production Example 1.

Comparative Example 1

An insulating layer was fabricated in the same manner as in Example 1, except that the melamine derivative produced in Production Example 1 was not added.

Comparative Example 2

An insulating layer was fabricated in the same manner as in Example 1, except that 4 parts by weight of melamine (Sigma Aldrich) was used instead of the melamine derivative produced in Production Example 1. As a result, the melamine was not dissolved and the coating was not uniform, and hence evaluation could not be performed.

Fabrication of Multiple Printed Circuit Board

Example 4

On the upper surface of the insulating layer fabricated in Example 1, a metal thin film was formed by depositing titanium (Ti) metal and copper (Cu) metal to thicknesses of 50 nm and 0.5 μm, respectively, through a sputtering process while supplying a mixture gas of argon and oxygen by a deposition system.

Thereafter, a photosensitive resin layer was formed on the metal thin film, exposed and developed to form a patterned photosensitive resin layer. In addition, a metal substrate made of copper was formed on the metal thin film through electroplating. Next, the patterned photosensitive resin layer was removed using a photosensitive resin stripper solution, and the seed layer exposed by removal of the patterned photosensitive resin layer was etched out to form a patterned metal layer on the insulating layer, thereby fabricating a multilayer printed circuit board.

Examples 5 and 6 and Comparative Example 3

A multilayer printed circuit board of Example 5 was fabricated in the same manner as in Example 4, except that the insulating layer fabricated in Example 2 was used instead of the insulating layer fabricated in Example 1.

In addition, a multilayer printed circuit board of Example 6 was fabricated in the same manner as in Example 4, except that the insulating layer fabricated in Example 3 was used.

In addition, a multilayer printed circuit board of Comparative Example 3 was fabricated in the same manner as in Example 4, except that the insulating layer fabricated in Comparative Example 1 was used.

Measurement of Metal Adhesion

The multilayer printed circuit boards fabricated in Examples 4 to 6 and Comparative Example 3 were left to stand at 135° C. and a humidity of 85% for 48 hours, and then the peel strength of the patterned metal layer in each of the multilayer printed circuit boards was measured according to the IPC-TM-650 standard and recorded as metal adhesion.

Table 1 below shows the results of measuring the metal adhesion between the insulating layer and the patterned metal layer in each of the multilayer printed circuit boards fabricated in Examples 4 to 6 and Comparative Example 3.

TABLE 1

|  | Metal adhesion (kgf/cm) |
|---|---|
| Example 4 | 0.51 |
| Example 5 | 0.54 |
| Example 6 | 0.52 |
| Comparative Example 3 | 0.22 |

Referring to Table 1 above, it can be confirmed that the metal adhesions of the multilayer printed circuit boards of Examples 4, 5 and 6, fabricated using the insulating layers of Examples 1, 2 and 3, respectively, which contained the melamine derivative, were excellent at 0.51 kgf/cm, 0.54 kgf/cm and 0.52 kgf/cm, respectively. However, it can be confirmed that the multilayer printed circuit board of Comparative Example 3, fabricated using the insulating layer of Comparative Example 1, which did not contain the melamine derivative, had very low metal adhesion. That is, it can be confirmed that the multilayer printed circuit board according to one embodiment of the present disclosure has excellent adhesion between the insulating layer and the patterned metal layer, suggesting that the melamine derivative has an effect of improving the adhesion

EXPLANATION OF REFERENCE NUMERALS AND SYMBOLS

100: Subtrate
200, 201, 202: Polymer resin layer
300: Patterned layer

What is claimed is:

1. An insulating layer for a multilayer printed circuit board, the insulating layer comprising a patterned polymer resin layer containing an alkali-soluble resin, a thermosetting binder, and a melamine derivative, wherein the melamine derivative has a structure of the following Chemical Formula 1:

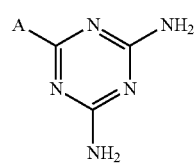

[Chemical Formula 1]

wherein A is an alkyl group containing 1 to 6 carboxyl groups, or an amine group containing 2 to 6 carboxyl groups.

2. The insulating layer of claim 1, wherein the patterned polymer resin layer contains the melamine derivative in an amount of 3 to 30 parts by weight based on 100 parts by weight of the alkali-soluble resin.

3. The insulating layer of claim 1, wherein the melamine derivative has a solubility of 5 to 20 in an aprotic solvent at 25° C.

4. The insulating layer of claim 1, wherein the alkali-soluble resin contains: one or more acidic functional groups; and a cyclic imide functional group substituted with one or more amino groups.

5. The insulating layer of claim 1, wherein the thermosetting binder contains an epoxy group and one or more functional groups selected from the group consisting of an oxetanyl group, a cyclic ether group, a cyclic thioether group, a cyanide group, a maleimide group and a benzoxazine group.

6. A multilayer printed circuit board comprising: the insulating layer according to claim 1; and a patterned metal layer positioned on the insulating layer.

7. The multilayer printed circuit board of claim 6, wherein the patterned metal layer has a peel strength of 0.4 kgf/cm to 1.2 kgf/cm, as measured according to the IPC-TM-650 standard after the multilayer printed circuit board is left to stand at a temperature of 135° C. and a humidity of 85% for 48 hours.

8. A method for fabricating the insulating layer of claim 1, the method comprising steps of:
   forming, on a substrate, a polymer resin layer containing an alkali-soluble resin, a thermosetting binder and a melamine derivative;
   forming a patterned layer on the polymer resin layer;
   developing and curing the polymer resin layer having the patterned layer formed thereon; and
   forming a patterned polymer resin layer by removing the patterned layer from the cured polymer resin layer,
   wherein the melamine derivative has a structure of the following Chemical Formula 1:

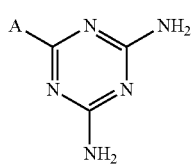

wherein A is an alkyl group containing 1 to 6 carboxyl groups, or an amine group containing 2 to 6 carboxyl groups.

9. The method of claim 8, wherein the step of forming the patterned layer on the polymer resin layer comprises steps:
   forming a photosensitive resin layer on the polymer resin layer; and
   forming the patterned layer by exposing the photosensitive resin layer and alkali-developing an unexposed portion of the photosensitive resin layer.

10. The method of claim 8, wherein the removing of the patterned layer is performed by treatment with a photoresist stripper solution.

11. The insulating layer of claim 4, wherein the acidic functional groups include a carboxyl group or a phenol group.

12. The insulating layer of claim 4, wherein the cyclic imide functional group substituted with one or more amino groups include at least two amino groups and at least two cyclic imide groups.

13. An insulating layer for a multilayer printed circuit board, the insulating layer comprising a patterned polymer resin layer containing an alkali-soluble resin, a thermosetting binder, and a melamine derivative, wherein the melamine derivative has a structure of the following Chemical Formula 1:

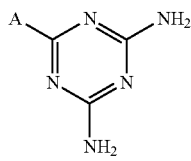

wherein A is an alkyl group containing 1 to 6 carboxyl groups, or an amine group containing 1 to 6 carboxyl groups,
wherein the alkali-soluble resin contains: one or more acidic functional groups; and a cyclic imide functional group substituted with one or more amino groups, and
wherein the cyclic imide functional group substituted with one or more amino groups include a functional group represented by the following Formula 1:

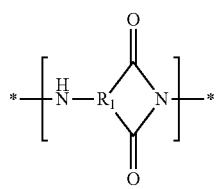

wherein $R_1$ is an alkylene group or alkenyl group having 1 to 10 carbon atoms, or 1 to 5 carbon atoms, or 1 to 3 carbon atoms, and "*" represents a bonding point.

14. An insulating layer for a multilayer printed circuit board, the insulating layer comprising a patterned polymer resin layer containing an alkali-soluble resin, a thermosetting binder, and a melamine derivative, wherein the melamine derivative has a structure of the following Chemical Formula 1:

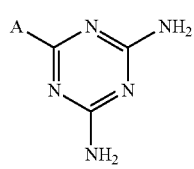

wherein A is an alkyl group containing 1 to 6 carboxyl groups, or an amine group containing 1 to 6 carboxyl groups,
wherein the alkali-soluble resin contains: one or more acidic functional groups; and a cyclic imide functional group substituted with one or more amino groups, and
wherein the cyclic imide functional group substituted with one or more amino groups include a functional group represented by the following Formula 2:

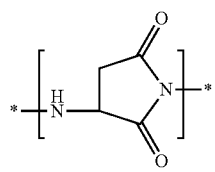

wherein "*" represents a bonding point.

15. An insulating layer for a multilayer printed circuit board, the insulating layer comprising a patterned polymer resin layer containing an alkali-soluble resin, a thermosetting binder, and a melamine derivative, wherein the melamine derivative has a structure of the following Chemical Formula 1:

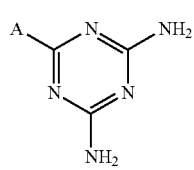

wherein A is an alkyl group containing 1 to 6 carboxyl groups, or an amine group containing 1 to 6 carboxyl groups, wherein the alkali-soluble resin includes at least one repeating unit represented by the following Formula 3 and at least one repeating unit represented by the following Formula 4:

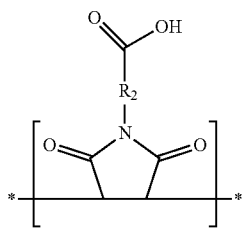

[Formula 3]

wherein $R_2$ is a direct bond, an alkylene group having 1 to 20 carbon atoms, an alkenyl group having 1 to 20 carbon atoms, or an arylene group having 6 to 20 carbon atoms, and "*" represents a bonding point,

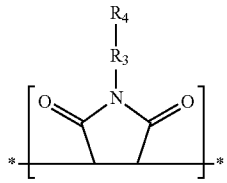

[Formula 4]

wherein $R_3$ is a direct bond, an alkylene group having 1 to 20 carbon atoms, an alkenyl group having 1 to 20 carbon atoms, or an arylene group having 6 to 20 carbon atoms, $R_4$ is —H, —OH, —$NR_5R_6$, a halogen, or an alkyl group having 1 to 20 carbon atoms, $R_5$ and $R_6$ may be each independently hydrogen, an alkyl group having 1 to 20 carbon atoms, or an aryl group having 6 to 20 carbon atoms, and "*" represents a bonding point.

* * * * *